United States Patent
Ringermacher et al.

(10) Patent No.: US 6,367,969 B1
(45) Date of Patent: Apr. 9, 2002

(54) SYNTHETIC REFERENCE THERMAL IMAGING METHOD

(75) Inventors: Harry I. Ringermacher, Delanson; Donald R. Howard, Troy, both of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/568,053

(22) Filed: May 10, 2000

Related U.S. Application Data

(60) Provisional application No. 60/144,886, filed on Jul. 21, 1999.

(51) Int. Cl.[7] ............................................... G01N 25/72
(52) U.S. Cl. .......................... 374/7; 374/5; 250/341.6; 250/330
(58) Field of Search ........................ 374/4–7; 250/341.6, 250/330, 332

(56) References Cited

U.S. PATENT DOCUMENTS

| | | |
|---|---|---|
| 4,768,158 A | 8/1988 | Osanai |
| 4,792,683 A | 12/1988 | Chang et al. |
| 4,854,724 A | 8/1989 | Adams et al. |
| 5,032,727 A | 7/1991 | Cox, Jr. et al. |
| 5,246,291 A | 9/1993 | Lebeau et al. |
| 5,250,809 A | 10/1993 | Nakata et al. |
| 5,292,195 A | 3/1994 | Crisman, Jr. |
| 5,539,656 A | 7/1996 | Annigeri et al. |
| 5,582,485 A | 12/1996 | Lesniak |
| 5,631,465 A | 5/1997 | Shepard |
| 5,683,181 A | 11/1997 | Shepard |
| 5,711,603 A | 1/1998 | Ringermacher et al. |

FOREIGN PATENT DOCUMENTS

| | | |
|---|---|---|
| EP | 304 708 | 3/1989 |
| EP | 0348742 | 6/1989 |
| GB | 2 168 494 | 6/1986 |
| GB | 2199942 | 1/1987 |
| GB | 2 220 065 | 12/1989 |
| GB | 2275773 | 2/1994 |
| JP | 10 274 675 | 10/1998 |
| WO | 98/05921 | 2/1998 |
| WO | 98/05949 | 2/1998 |

OTHER PUBLICATIONS

Becker et al., Method of Determining The Wall Thickness of a Turbine Blade and Device for Carrying out This Method, English Translation (PTO 01–927) of WO 98/05921 A1, Feb. 1998.*

Article entitled "Thermal NDE System", Aerospace Engineering, Oct. 1995, p. 7.

Article entitled "Thermal Evaluation Reveals Depth Detail", Photonics Spectra, Jun. 1995, pp. 21–22.

Ringermacher, H.I. et al., "Towards a Flat–Bottom Hole Standard for Thermal Imaging", Review of Progress in Quantitative Nondestructive Evaluation, vol. 17A, Edited by D.O. Thompson and D.E. Chimenti, Plenum Press, New York, May 1998, pp. 425–429.

\* cited by examiner

Primary Examiner—Diego Gutierrez
Assistant Examiner—Stanley J. Pruchnic, Jr.
(74) Attorney, Agent, or Firm—Nixon & Vanderhye PC

(57) ABSTRACT

In an infrared (IR) transient thermography system a sequence of image frames is acquired from an IR sensitive focal-plane array camera. Each sequentially acquired image frame is made up of an array of pixels and has assigned a frame number that corresponds to elapsed time. A method of analyzing thermal imaging data-frames is presented wherein a synthetically generated temperature-time reference curve is used to determine pixel contrast-versus-time data.

12 Claims, 3 Drawing Sheets

SYNTHETIC REFERENCE THERMAL IMAGING METHOD

This application claims the benefit of U.S. Provisional Application No. 60/144,886, filed Jul. 21, 1999 the entire content of which is hereby incorporated by reference in this application.

TECHNICAL FIELD

The present invention relates to thermographic nondestructive testing techniques for determining the thickness of an object. More particularly, the present invention relates to a infrared transient thermography method that utilizes a synthetic thermal reference in determining the wall thickness of metal turbine rotor blades or the like.

BACKGROUND

Over the years, various nondestructive ultrasonic measurement techniques have been utilized to determine cross-sectional thickness of cast metal and other solid objects. Conventionally, the object is probed with ultrasonic waves which penetrate the surface and are reflected internally at the opposite side or surface of the object. Based upon the time required to receive a reflected wave, the distance to the opposite (back) side can be determined—giving the thickness of the object at that point. Unfortunately, conducting ultrasonic measurements of this sort to examine the cross-sectional thickness for most of an object would usually necessitate a cumbersome and time-consuming mechanical scanning of the entire surface with a transducer. In addition, to facilitate intimate sonic contact between the transducer and the object surface, a stream of liquid couplant must be applied to the surface or, alternatively, total immersion of the object in the couplant must be accommodated. Such accommodations, however, are most often not very practical or even feasible for numerous structural and material reasons. For example, ultrasonic systems capable of scanning and analyzing geometrically complex parts are typically very expensive and complicated. In addition, a mechanical scanning of the transducer over the surface of a large object can literally take hours.

Moreover, when conducting ultrasonic measurements on certain metal objects, the internal crystal orientation and structure of the metal can cause undesirable noise and directional effects that contribute to inaccuracies in the acquired data. This inherent limitation of ultrasonic measurements proves to be a serious drawback when testing components constructed of crystalline or "directional" metals such as often used in contemporary turbine airfoils.

In contrast, infrared (IR) transient thermography is a somewhat more versatile nondestructive testing technique that relies upon temporal measurements of heat transference through an object to provide information concerning the structure and integrity of the object. Since heat flow through an object is substantially unaffected by the micro-structure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour or shape of the object being tested and, moreover, can be accomplished ten to one-hundred times faster than most conventional ultrasonic methods if testing objects of large surface area.

One known contemporary application of transient thermography, which provides the ability to determine the size and "relative" location (depth) of flaws within solid non-metal composites, is revealed in U.S. Pat. No. 5,711,603 to Ringermacher et al., entitled "Nondestructive Testing: Transient Depth Thermography"; and is incorporated herein by reference. Basically, this technique involves heating the surface of an object of interest and recording the temperature changes over time of very small regions or "resolution elements" on the surface of the object. These surface temperature changes are related to characteristic dynamics of heat flow through the object, which is affected by the presence of flaws. Accordingly, the size and a value indicative of a "relative" depth of a flaw (i.e., relative to other flaws within the object) can be determined based upon a careful analysis of the temperature changes occurring at each resolution element over the surface of the object. Although not explicitly disclosed in the above referenced Ringermacher patent, the "actual" depth of a flaw (i.e., the depth of a flaw from the surface of the object) can not be determined unless a "standards block", having voids at known depths, or an "infinite" (thermally thick) reference region on the object is included as part of the thermographic data acquisition and analysis for comparison against the relative depth values.

To obtain accurate thermal measurements using transient thermography, the surface of an object must be heated to a particular temperature in a sufficiently short period of time so as to preclude any significant heating of the remainder of the object. Depending on the thickness and material characteristics of the object under test, a quartz lamp or a high intensity flash-lamp is conventionally used to generate a heat pulse of the proper magnitude and duration. However, the specific mechanism used to heat the object surface could be any means capable of quickly heating the surface to a temperature sufficient to permit thermographic monitoring—such as, for example, pulsed laser light. Once the surface of the object is heated, a graphic record of thermal changes over the surface is acquired and analyzed.

Conventionally, an infrared (IR) video camera has been used to record and store successive thermal images (frames) of an object surface after heating it. Each video image is composed of a fixed number of pixels. In this context, a pixel is a small picture element in an image array or frame which corresponds to a rectangular area, called a "resolution element", on the surface of the object being imaged. Since, the temperature at each resolution element is directly related to the intensity of the corresponding pixel, temperature changes at each resolution element on the object surface can be analyzed in terms of changes in pixel contrast. The stored IR video images are used to determine the contrast of each pixel in an image frame by subtracting the mean pixel intensity for a particular image frame, representing a known point in time, from the individual pixel intensity at that same point in time.

The contrast data for each pixel is then analyzed in the time domain (i.e., over many image frames) to identify the time of occurrence of an "inflection point" of the contrast curve data, which is mathematically related to a relative depth of a flaw within the object. Basically, as applied to an exemplary "plate-like" object of consistent material and thickness L, a heat flux pulse impinging on an object takes a certain "characteristic time", $T_c$, to penetrate through the object to the opposite side (back wall) and return to the front surface being imaged. This characteristic time, $T_c$, is related to the thickness of the object, given the thermal diffusivity of the material, by the following equation:

$$T_c = 4L^2/\pi^2 \alpha \qquad \text{Equ.(1)}$$

where L is the thickness (cm) of the object and $\alpha$ is the thermal diffusivity (cm²/sec) of the material.

From empirical observations it is known that after a heat pulse impinges on a plate-like object, the surface temperature observed from the same side of the object (i.e., the front) rises in a fashion that is also dependent on the thickness and the thermal diffusivity of the material. Moreover, from a graph of the time vs. temperature (T-t) history of the surface, one can determine the characteristic time, $T_c$, in terms of a unique point on the T-t curve, called the "inflection point." This inflection point, $t_{infl}$, is indicated by the point of maximum slope on the T-t curve (i.e., peak-slope time) and is related to the characteristic time, $T_c$, by the following equation:

$$t_{infl}=0.9055\ T_c \qquad \text{Equ.(2)}$$

This relationship between the inflection point and the characteristic time, as expressed by Equ. (2) above, is precise to approximately 1% for one-dimensional (1-D), as well as two-dimensional (2-D), heat flow analysis. Once an inflection point, $t_{infl}$, is determined from the T-t response, a relative thickness, L, of the object can be determined from Equ. (1) using the known thermal diffusivity, $\alpha$, of the material and the actual value of $T_c$ from Equ. (2).

In this regard, a more detailed discussion of the heat-flow invariant relationship between the peak-slope time (inflection point) and the material "characteristic time" as defined above may be found in the *Review Of Progress In Quantitative Nondestructive Evaluation*, in an article by Ringermacher et al., entitled "Towards A Flat-Bottom Hole Standard For Thermal Imaging", published May 1998 by Plenum Press, New York, which is incorporated herein by reference.

Unfortunately, the above mentioned apparatus and method of U.S. Pat. No. 5,711,603 to Ringermacher et al. only produces "relative" depth measurements. It can not be used to obtain a value for the actual thickness of a metal object at a desired point. Consequently, a better method of conducting and processing IR transient thermography that would permit a determination of the actual thickness of metal objects was needed. One such method and apparatus is disclosed in a commonly assigned co-pending U.S. patent application (Ser. No. 09/292,886) of Ringermacher et al. filed Apr. 4, 1999. Basically, the arrangement disclosed therein utilizes a focal-plane array camera for IR image data acquisition and high-power flash lamps to rapidly heat the surface of a desired examined object. A slab object of similar material having portions of known thickness is used as a "infinite half-space" reference standard within the same image frame (a "thermally thick" section of the examined object may optionally be used as the reference). The flash-lamp are fitted with spectrally tuned optical filters that minimize long-wave IR "afterglow" emissions and reduce background radiation effects which affect the accuracy of thermal measurements. A predetermined number of IR image frames are acquired and recorded over a predetermined period of time after firing the flash-lamps to develop a temperature-time (T-t) history of the object surface (and the reference standard). Contrast versus time data is then developed for each pixel in the image to determine object thickness at a location corresponding to the pixel position.

In the above method contrast-time data is developed by subtracting temperature-time data of the slab reference standard (or temperature-time data of a "deep" thermally thick reference region on the object) from the temperature-time data of each pixel. Unfortunately, this method suffers from the disadvantage that it may introduce some degree of error when imaging objects that have varying surface uniformity. Moreover, it requires the presence of a slab standard in the image or the use of temperature-time data from a deep reference region on the object—assuming such a reference region is available. In addition, a special coating must usually be applied to the surface of the object (and the slab standard) prior to imaging to enhance optical absorption and improve surface uniformity.

DISCLOSURE OF THE INVENTION

The present invention relates to a nondestructive testing method and apparatus for determining and displaying the actual thickness of an object through the use of high speed infrared (IR) transient thermography. An improved high-speed IR transient thermography analysis approach is utilized to accurately measure the thickness of an object and provide a visual coded display indicative of its cross-sectional thickness over a desired area of the object. A salient feature of the present invention is that a "synthetic" or computed reference, based on actual surface temperature, is used to compute the contrast versus time data needed to determine thickness. Consequently, at least one beneficial aspect of the present invention is that is does not require the use of a separate reference standard or a reference region on the examined object. In addition, when using the transient thermographic technique of the present invention there is no need to apply special coatings to the object(s) being examined. Moreover, the method of the present invention can readily accommodate objects having non-uniform surfaces or varying surface emissivity.

Basically, the present invention makes use of an inflection point in a temperature-time (T-t) response analysis of the surface of a rapidly heated object, preferably obtained from "front-side" IR camera observations. This inflection point, $t_{infl}$, occurs relatively early in the T-t response and is essentially independent of lateral heat loss mechanisms. (Such considerations may be of particular relevance, for example, when working with metals since, due to the high thermal conductivity of metals, the thermal response of a metal object is fairly quick and, consequently, the time available for obtaining thermal data measurements is usually short). The inflection point, $t_{infl}$, is extracted from thermal data acquired over a predetermined time period from successive IR camera image frames. Preferably, this time period is at least somewhat longer than an anticipated characteristic time, as obtained from Equ.(1), based on an estimation of the thickness of the object being evaluated.

In accordance with the present invention, the inflection point, $t_{infl}$, is determined by utilizing pixel contrast data that is based on a "synthetic" or computed thermal reference instead of a "real" reference such as a slab standard or a suitable region on the examined object. This computed synthetic reference represents the surface temperature of an object as a function of time for one-dimensional heat flow into a semi-infinite medium (half-space) and is given by the following relationship:

$$T_s(t)=A[t^{1/2}-(t-\tau)^{1/2}] \qquad \text{Equ.(3)}$$

where $T_s(t)$ is the surface temperature of the synthetic thermal reference as a function of time t, A is a parameter selected to match actual surface temperature on an object surface at a location corresponding to a selected analysis pixel in an acquired IR image, and $\tau$ is a duration of heating the object before acquiring image frames.

Essentially, the reference temperature-time data provided by Equ. (3) describes a "synthetic" half-space thermal decay based on an initial temperature, A, at a particular location on the surface of the object. As described in greater detail below, the "synthetic" thermal reference data as obtained from Equ. (3) is first computed for each (x,y) pixel location of the imaged object and then used to determine contrast as a function of time for each pixel. Moreover, as a further advantage, determination of the synthetic thermal reference data is not dependent upon the nature or characteristic of the particular material or metal being evaluated—as it is not a parameter in Equ. (3).

As illustrated by FIG. 1, the apparatus accordance of the present invention includes an imaging system comprising one or more high power flash lamps fitted with special optical filters, an IR sensitive focal-plane array camera for data acquisition and a display monitor. A computer system controls the imaging system, records and analyzes surface temperature data acquired via the IR camera and provides a color or gray pattern-keyed image on the display monitor that accurately corresponds to thickness of the object.

The acquisition of surface temperature data is initiated by firing the flash-lamps to illuminate the surface of the object. The special optical filters are spectrally tuned to absorb and/or reflect all 3–5 micron IR radiation back into the flash-lamp(s). This prevents undesirable long-wave IR "afterglow" emissions—typically generated by overheated metallic elements in the flash-lamps after the lamps are extinguished—from reaching the object or the camera. The use of such filters enables a more precise thermal evaluation that can produce dimensional measurements within an accuracy range of 1%–3% of actual thickness.

A predetermined number of image frames are then recorded over a period of time after the flash lamps are fired and the recorded images used to develop a temperature-time (T-t) history for every elemental region or "resolution element" over the region of interest on the object surface. Each recorded image frame is comprised of a predetermined n×m array of image pixels whose intensity correlate to the surface temperature of the object at the time the frame data was acquired—each pixel having an (x,y) location designation within the image frame that corresponds to a particular resolution element.

A heat flow analysis of the T-t history is then conducted for each pixel in the acquired image frames to determine the thickness of the object at each resolution element location. Conventionally, analysis of transient heat flow through solid portions of an object requires determining a characteristic time, $T_c$, required for a "pulse" of thermal energy to penetrate the object at a first surface, reflect off an opposite surface and return to the first surface. Since this characteristic time is related to the distance between the two surfaces, it can be used to determine the thickness of the object between the two surfaces at a desired point. Because $T_c$ is also related in time to the occurrence of an inflection point, $t_{infl}$, in the contrast-versus-time data history of a pixel according to Equ. (2) above, a value for characteristic time $T_c$ may be determined by using a recorded intensity-versus-time history of the pixel to compute contrast-versus-time data for the pixel—which in the present invention is accomplished by subtracting the "synthetic" thermal reference T-t data from the recorded intensity-versus-time data of the pixel.

Using the synthetic thermal reference, a contrast-versus-time curve is determined for each (x,y) pixel location corresponding to each resolution element of the object surface. Next, Gaussian temporal smoothing of the pixel contrast curve data is employed to improve the signal-to-noise ratio of the measurements. The mathematical derivative of the contrast curve is then computed to identify an inflection point in the data. This derivative is preferably computed using a three-point data sampling having a first and third sample point separation that is proportionally related to the value of the image frame number at the second sample point. Next, all local "peaks" in the contrast curve obtained from the derivative computation are identified and a weighting function is used as a filter to adjust the significance of localized each of these peaks to identify the actual inflection point in the T-t contrast curve data for use in determining object thickness. Finally, thickness of the object at a location corresponding to each pixel is quantitatively determined according to Equ. (1) and Equ. (2) above.

BRIEF DESCRIPTION OF THE DRAWINGS

The purpose and advantages gained by the present invention will be understood by careful study of the following detailed description of the presently preferred embodiment with particular reference to the accompanying drawings.

BEST MODE FOR CARRYING OUT THE INVENTION

Figure 1:
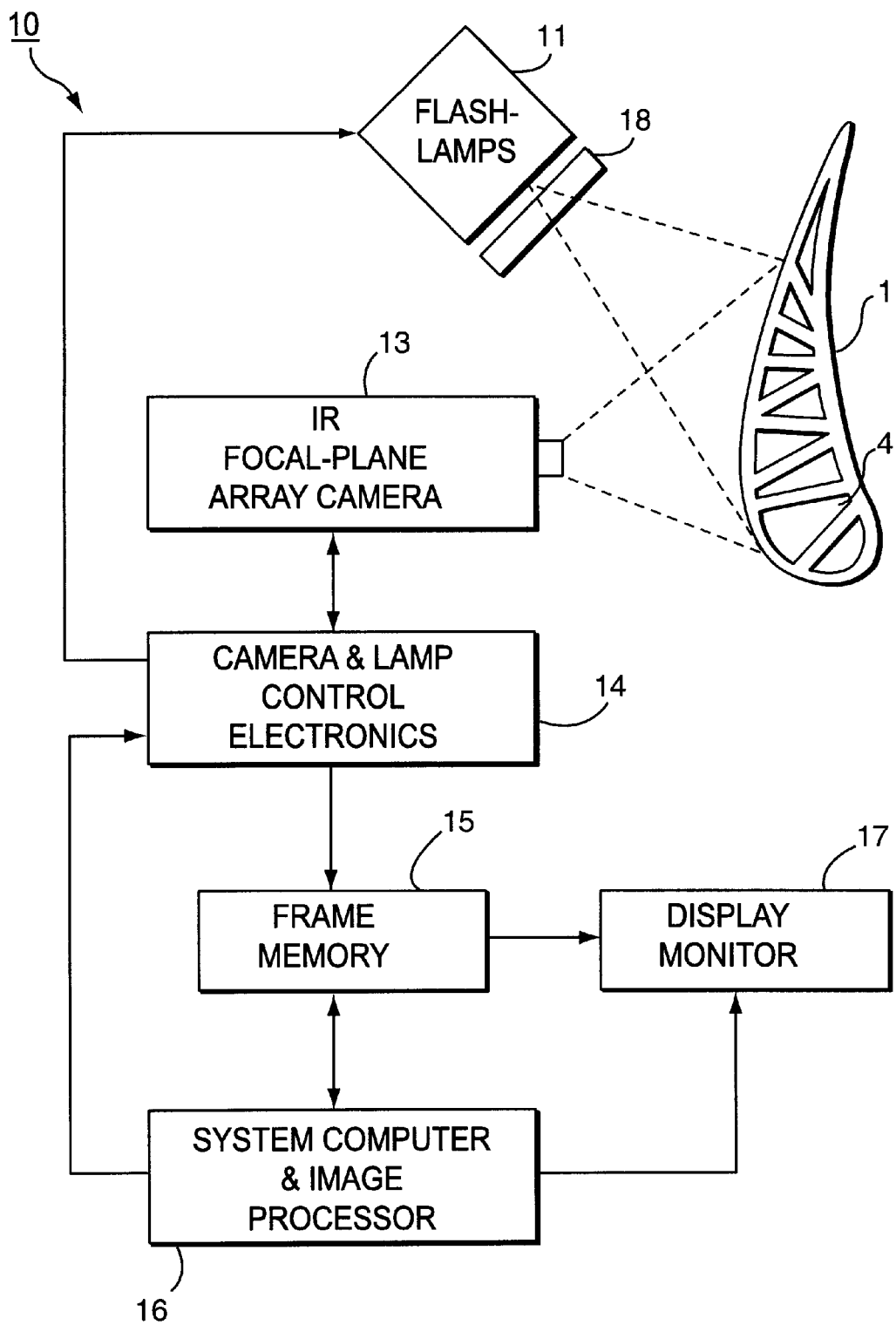
FIG. 1 is schematic diagram illustrating an example infrared transient thermography system arrangement for determining and displaying the actual thickness of an object in accordance with the present invention.

FIG. 1 illustrates an example IR transient thermography system 10 for determining and displaying the thickness of an object, e.g., a metal turbine airfoil 1 having intentional voids 4. For the purposes of the following discussion, the "thickness" of an object refers to a front wall or surface thickness in the context of a hollow or semi-hollow object (i.e., an object having an intentional void).

As shown in FIG. 1, a flash-lamp heat-pulse source 11 is used to rapidly heat the surface of the object being measured. One suitable arrangement for flash-lamp heat-pulse source 11 would be, for example, a set of four or eight high-speed, high output power photographic flash-lamps, each capable of about 4.8 Kilo-joules output and having individual power supplies (such as, for example, flash-lamps manufactured by Speedotron, Corp. in Chicago, Ill.).

Since metals have a significantly faster rate of heat conduction than non-metals, the characteristic times for heat flow in metals are much faster than those of, for example, plastic or composite materials. Consequently, in attempting to adapt conventional IR thermography techniques (ordinarily limited to non-metals) to metals, a sharp cutoff in the applied heat is needed. In order to obtain this, a 3–5 micron reflective filter 18 is used between (covering) flash-lamps 11 and object of interest 1 so as to prevent exposing the object to residual heat as the flashlamps cool down after exposure.

In practice, one or more filters may be used (e.g., one per each flash-lamp). These filters act to prevent direct long wave radiation X typically generated from the "afterglow" of overheated metallic elements in the flash-lamps X from ever leaving the flash-lamps and impinging on the target or otherwise reflecting back into focal-plane array camera 13.

Such primary afterglow radiation from flash-lamps 11 competes and can interfere with the long-wave IR emissions from the targeted object during early thermal data acquisition, thus obscuring the true target-generated JR radiation and reducing ultimate image contrast and quality. Thus, the use of these special filters produces a sufficiently sharp heat pulse to enable the shorter heat travel time in metal to be detected.

In the example embodiment depicted in FIG. 1, flash-lamp filter 18 may be composed of Pyrex™, fused quartz, BK7™, or other optical material that is transparent to visible and UV light and is coated on the flash-lamp facing side with an infrared-reflective coating to reflect all radiation in the 3–5 micron range back into the flash-lamps. (Optical glass and coated filters may be acquired or specially manufactured by a general scientific optics and optical glass manufacturer such as, for example, Oriel in Stratford, Conn.).

Surface temperature measurements of heat-pulse illuminated object 1 are acquired using a infrared (IR) sensitive imaging system comprising an IR sensitive focal-plane array camera 13 (e.g., a Radiance HS camera may be available from Amber Engineering in Goleta, Calif.—a Raytheon Company), control electronics 14, frame data memory 15, control computer/image processor 16 and display monitor 17.

Acquisition of thermal data is preferably initiated at the time of flash lamp firing either by optical triggering or by other suitable means. Flash-lamp firing is controlled via conventional flash-lamp electronics 14 managed by conventional video frame acquisition software running on system computer 16 (such as provided by the Image Desk™ frame acquisition system from Amber Corp. or other conventional frame acquisition and flash-lamp control software, for example, such as commercially available from Thermal Wave Imaging Inc. in Lathrup Village, Mich.).

The system control computer/image processor 16 is a specially programmed general purpose digital computer that is capable of peripheral equipment control and communication functions in addition to digital image processing and display in accordance with the method of the present invention. System computer 16 controls camera and lamp electronics 14 and frame data memory 15 to acquire a predetermined number of successive thermal image frames of the object surface which are stored in memory 15 for future analysis.

Before beginning the thermal imaging process, IR camera 13 is first calibrated using a "full-field" dual-image calibration technique as now described. This preferred technique employs two "black-body" (BB) image calibration references: a BB "cold" source using a room-temperature flat-black plate and a BB "hot" source using a heated flat-black plate. For example, for acquiring the BB "cold" source calibration image, a flat-black painted box enclosing the room-temperature flat-black plate, arranged at a 45° angle to the camera lens, is placed directly in front of the lens. For acquiring the BB "hot" source calibration image, the camera lens is placed into the same flat-black painted box unit after heating the flat-black plate—nominally to about 10° C. above ambient—such that the camera images the heated plate over its full field. Although the above described dual-image calibration technique is preferred, any calibration technique that results in producing maximum uniformity of the image field—which is important for high contrast imaging and obtaining improved thermal accuracy—can be used.

Each image frame acquired during the imaging process consists of N×N pixels—each pixel corresponding to a resolution element on the object surface—where N is typically either 128 or 256 depending on the resolution and accuracy desired. Each pixel occupies about two bytes of storage memory and may be represented, for example, by a 12-bit or larger binary number. The stored image frames are sequentially identified with increasing frame number values which together serve to provide a historical record of the temperature vs. time (T-t) characteristics of a front surface of object 1 for a predetermined period after being struck by the heat impulse imparted by flash lamp 11.

During evaluation of a metal object, after control computer 16 triggers the firing of flash-lamp(s) 11, image data frames are acquired from camera 13 and the IR intensity at each resolution element on the image is digitally recorded and stored in frame data recorder 15. Data acquisition continues over a predetermined number of sequential image frames that are sufficient to acquire a meaningful T-t history over a duration of at least one estimated "characteristic time" for the material of the object. The total number of image frames acquired may vary depending on the accuracy and image resolution desired and can be as high as 550 frames per second of data acquisition.

Frame data recorder 15 may be a conventional digital memory internal to processor 16 or any suitable video frame data storage device accessible by processor 16. Each successive thermal image frame acquired is assigned an increasing frame number, Z, corresponding to the passage of real time. The resulting data frame "stack" is then analyzed taking a one-dimensional heat flow analysis approach, as outlined above. In accordance with this approach, the method of the present invention takes advantage of a known thermal invariance property—evidenced in the temperature vs. time (T-t) history of each image pixel over successive IR image frames X that relies on identifying the location of an "inflection point" or peak-slope time, i.e., the point in time of maximum slope on the T-t data curve.

Figure 2:
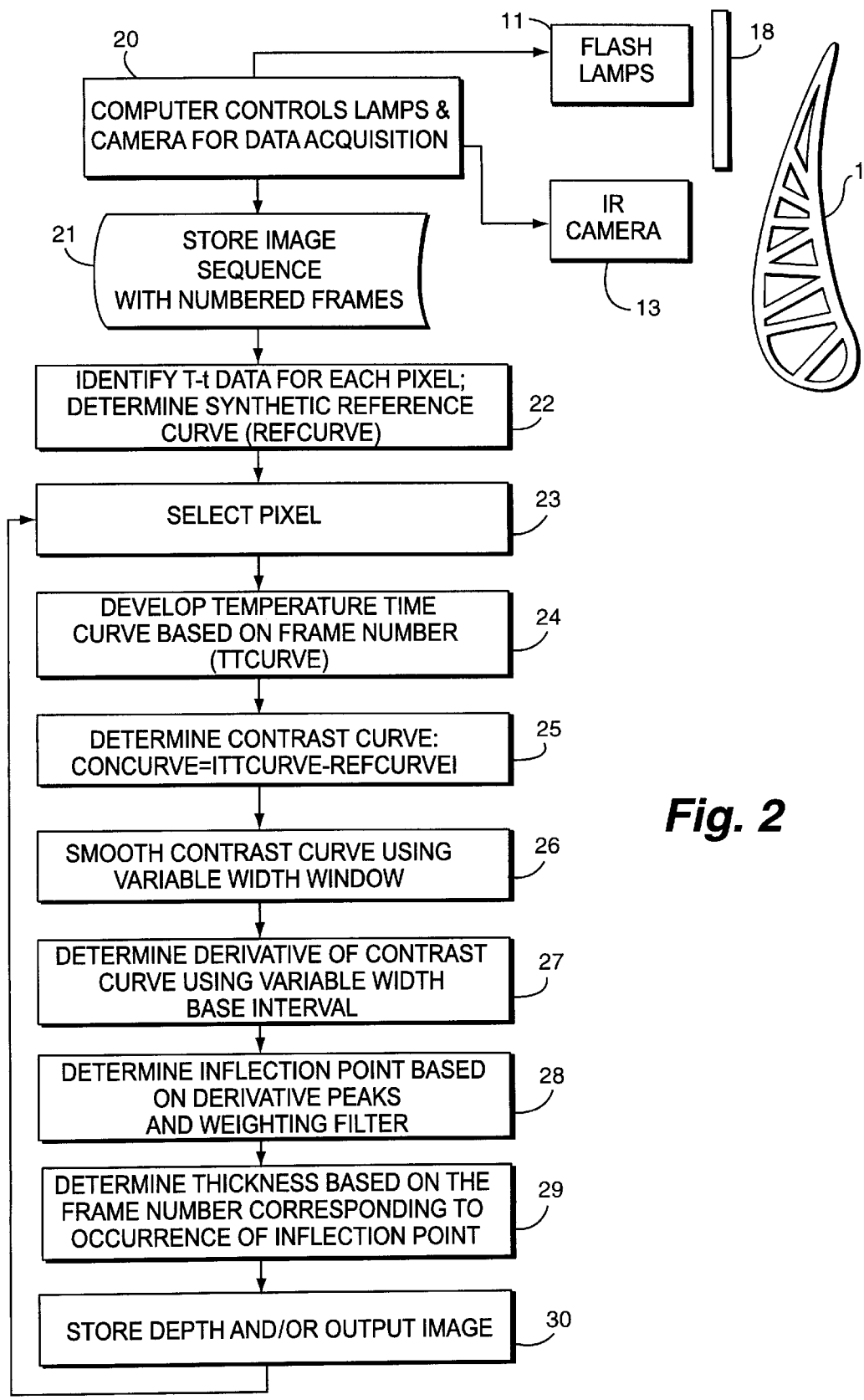
FIG. 2 is a flowchart illustrating the process of infrared image data acquisition and analysis as performed by the system of FIG. 1 in accordance with the present invention.

Referring now to FIG. 2, a flow diagram is presented that illustrates example processing steps for conducting transient IR thermography using synthetic-reference thermal imaging techniques of the present invention. These steps may be implemented, for example, by appropriately programming computer 16 (FIG. 1) using known conventional programming techniques.

Initially, as indicated at block 20, a region of interest on the object is identified (i.e., the IR camera is focused to capture the region of interest) and the system operator selects or inputs information concerning relevant parameters for examining the object such as, for example, a thermal diffusivity coefficient for the material. Next, as indicated at block 20 in FIG. 2, the system control computer instructs the flash-lamp electronics to fire flash-lamps 11 and initiate image frame data acquisition from the focal plane array IR camera 13. Data acquisition proceeds over a predetermined number of sequential image frames and then, as indicated at 21, the image sequence is stored in frame memory 15 after identifying each acquired image frame with a sequential frame number, Z.

Next, as indicated at 22, a set of T-t curve data is identified for each pixel in the thermal image corresponding to each resolution element location over the region of interest on the surface of the object. Also, a time and frame number of the initial IR "flash" heating is identified, a first unsaturated data frame is identified, and a "synthetic" half-space thermal decay T-t reference data curve (refcurve) is generated based upon an initial surface temperature parameter, A, and the flash duration, τ, according to Equ (3) as given above.

Equ. (3) is valid for times (t) greater than or equal to τ(the flash heating duration). Preferably, the parameter A is chosen to match the actual initial value of temperature as measured at a selected analysis pixel in the image. With this approach, the starting temperature for a synthetic thermal decay reference, thus generated, is rendered adjustable at each pixel without having to know the nature of the particular material being examined. Thus, if different pixels have varying starting temperatures, the generated synthetic reference of the present invention can accommodate such variations; whereas, a "real" slab standard thermal reference can not, since it is limited to a fixed-value starting temperature.

As indicated at 23 and 24, a first pixel (or the next pixel) is then selected for analysis and its T-t curve data (ttcurve) is developed from recorded pixel intensity data stored in frame memory 15. At this point, optional offset and scale (amplitude) adjustments can also be made at this step to help compensate for any derogatory effects such as, for example, loss of amplitude due to surface curvatures. Next, as indicated at 25, a contrast curve (concurve) is determined for the selected pixel by subtracting the synthetic reference T-t curve data (refcurve) from the T-t curve (ttcurve) data of the pixel.

As indicated at 26, a Gaussian function temporal smoothing of the contrast curve data may also be performed. In a preferred embodiment, a "temporal window" used in the Gaussian smoothing algorithm is made to vary as a function of time by making it proportional to the image frame number, Z, corresponding to the contrast data. Essentially, this smoothing "window" controls the full-width of the Gaussian at half-maximum (i.e., the "2-σ" width). Using a variable-width frame-number smoothing as described is more advantageous than a traditional Gaussian smoothing because it tends to compensate for the effects of heat diffusion at increasing depths within the material. Preferably, for this step, the width of the smoothing window at a selected data point is made proportional to the square-root of the image frame number at that point. In addition to the described variable-width frame-number Gaussian temporal smoothing, a number of software implemented "imaging filters" may also be applied to the contrast curve data at this stage, including spatial smoothing, initial and ending noise suppression, negative contrast suppression and contrast thresholding.

Next, at step 27, the mathematical derivative of the contrast curve, indicative of the inflection point, is determined. It is well known that the point of maximum slope on a curve can be determined by using a conventional 3-consecutive-point derivative algorithm in which three equally spaced consecutive data points along the curve are sampled and used to calculate the slope of the curve at the second (middle) data point. In accordance with the present invention, three points are still used to determine the derivative of the contrast curve, but the separation of the first and third sample derivative points (i.e., the width of the derivative base interval) is linked to real time in the image evolution via the image frame number. Specifically, the width of the derivative base interval at any selected point along the contrast curve is made proportional to the square-root of the IR image frame number, Z.

In this manner, the signal-to-noise (S/N) characteristics are maximized even in the midst of high noise levels. This improvement in the S/N ratio results from "sampling" over a larger interval and, thus, detects the largest signal change rather than the differential change traditionally obtained with fixed-width 3-point differentiation. Since a maximum S/N ratio is obtained when the sample point separation is equal to the full Gaussian width, the maximum possible SIN ratio is always achieved by using the frame-number proportional-width approach of the present invention.

Next, at step 28, all local peaks in the derivative curve are identified and a significance "weighting" factor is used to assess the proper peak to use as the $t_{infl}$ inflection point. During this step, a list of all peak location times (i.e., frame numbers) and amplitudes is maintained in computer memory. By applying a predetermined appropriate weighting function to the peak list, it is possible to adjust the significance of each peak so that, for example, peak-producing noise effects arising early in the data acquisition time are effectively discounted. Since empirical evidence indicates that peaks occurring later in time tend to be more significant, a temporal weighting function is implemented in the present example embodiment by simply multiplying the amplitude of a peak by the time at which it occurred. The peaks are then sorted according to decreasing significance (weight) and the peak having the greatest weighting value (i.e., the most significant) is selected as indicative of the proper inflection point.

Next, at step 29, the thickness of the object at the location of the resolution element corresponding to the selected pixel is determined. This is accomplished by identifying the frame number in which the most significant peak occurs, i.e., the inflection point $t_{infl}$, and converting that value to real time. Since acquisition of IR image frames occurs at a fixed predetermined rate, a frame number can be equated to a real elapsed time. Accordingly, the frame number of the IR image frame harboring the most significant peak in the derivative curve provides an actual quantitative time value for $t_{infl}$. Using this value for $t_{infl}$ in Equ. (1) and Equ. (2) above, provides a thickness value, L, denoting the actual thickness of the object at the location of the resolution element corresponding to the analyzed pixel.

Next, at step 30, the thickness value, L, is stored in memory and used to build a color-mapped or gray-scale image of the region of interest on the object surface for display or print—each color or gray shade corresponding to a particular thickness. The next pixel is then selected, as indicated at 23, and the above steps are reiterated for each pixel comprising the IR image.

In addition to the steps outlined above, the input and selection of various parameter values such as diffusivity constant, data analysis starting point and range, temporal smoothing window size range, and color mapping range are automated for accuracy and consistency through appropriate conventional programming of the system control computer.

By conducting the transient thermography analysis using the above described steps for thermal data acquisition and analysis in conjunction with the above described apparatus in accordance with the present invention, wall thickness values can be accurately obtained even between closely spaced back wall or internal structures that may form a part of, or be connected to, the tested object—e.g., the rib-like structures often found in turbine air foils (as depicted in FIG. 1)—whereas using traditional thermal or ultrasonic methods such closely positioned back-wall structures would normally result in blurred images and distorted data.

Figure 3:
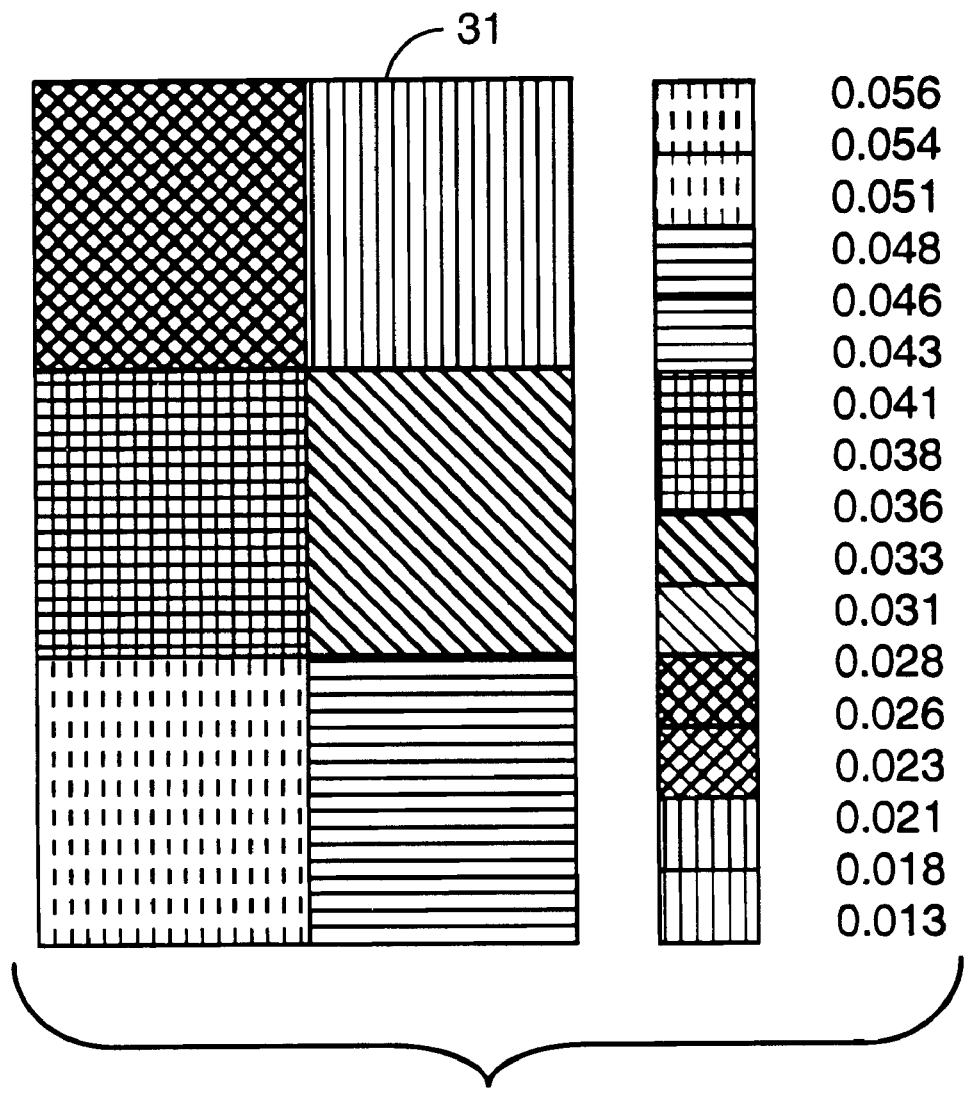
FIG. 3 is an example print of an infrared transient thermography image display of a nickel-alloy metal step-standard in accordance with the present invention.

In FIG. 3 a diagram of an infrared transient thermography display image for a multi-tiered object block is depicted. Object block 31 depicted in FIG. 3 has six square sections of different thickness. The thickness of each of the six sections is indicated by a different color or gray tone in the generated image (shown here as different cross-hatchings)

which corresponds to a like color or shade in a bar-scale thickness key displayed at the right of the image. In this example, the bar-scale includes indicia of thickness ranging from 0.013 to 0.056 inches, but a displayed bar-scale having a different range may also be used.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In an infrared (IR) transient thermography system wherein a sequence of image frames is acquired from an IR sensitive camera, each sequentially acquired image frame comprising an array of pixels and having assigned a frame number that corresponds to elapsed time, a method of analyzing thermal imaging data-frames wherein a synthetically generated temperature-time reference curve is used to determine pixel contrast versus time data.

2. The method of claim 1 wherein the synthetically generated temperature-time reference curve is calculated according to the following formula:

$$T_s(t)=A[t^{1/2}-(t-\tau)^{1/2}]$$

where A is a parameter selected to match actual temperature on an object surface at a location corresponding to a selected analysis pixel in an acquired IR image, $\tau$ is a duration of heating the object before acquiring image frames and t is time.

3. In an infrared (IR) transient thermography system wherein a sequence of image frames is acquired from an IR sensitive focal-plane array camera, each sequentially acquired image frame comprising an array of pixels and having assigned a frame number that corresponds to elapsed time, a method for determining contrast versus time data for a pixel, comprising the steps of:

(a) acquiring pixel IR intensity versus time data corresponding to a selected analysis pixel in an IR image of an object from a plurality of image frames; and (b) subtracting from said pixel intensity data a synthetic temperature time reference standard, $T_s(t)$, computed according to the following mathematical relationship:

$$T_s(t)=A[t^{1/2}-(t-\tau)^{1/2}]$$

where A is a parameter selected to match actual temperature on an object surface at a location corresponding to a selected analysis pixel in an acquired IR image, $\tau$ is a duration of heating the object before acquiring pixel IR intensity versus time data and t is time.

4. The IR transient thermography method of claim 3 wherein pixel IR intensity versus time data is based at least upon a sequence of IR images and associated frame numbers.

5. The IR transient thermography method of claim 3 further including the step of measuring a surface temperature on the object surface corresponding to said selected analysis pixel.

6. The IR transient thermography method of claim 3 wherein the object is rapidly heated using a flash lamp device.

7. A method for determining a thickness of an object having a surface which can be visualized as an array of pixels, comprising the steps of:

(a) rapidly heating the surface of an object;

(b) recording pixel intensity in a sequence of IR images, each image having an assigned sequential frame number related to time elapsed since heating the object surface in step (a);

(c) determining pixel contrast data based at least upon pixel intensity and a temperature-time reference standard, $T_s(t)$, computed according to the following mathematical relationship:

$$T_s(t)=A[t^{1/2}-(t-\tau)^{1/2}]$$

where A is a parameter selected to match actual temperature on an object surface at a location corresponding to a selected analysis pixel in an acquired IR image, $\tau$ is a duration of heating the object before acquiring image frames and t is time; and (d) determining thickness of the object based at least upon pixel contrast as determined in step (c) and an image frame number assigned in step (b).

8. The method of claim 7 further including the step of measuring a temperature on the object surface corresponding to said selected analysis pixel.

9. The method of claim 7 wherein the object is heated using a flash lamp device.

10. An infrared (IR) transient thermography method for determining a thickness of an object, comprising the steps of:

a) using an IR sensitive focal-plane array camera to acquire pixel intensity data from a sequence of IR image frames of the object, each image frame comprising a plurality of pixels and having an assigned sequential frame number related to time elapsed since heating the object surface;

b) calculating a temperature versus time data standard, $T_s(t)$, from a mathematical thermal reference model representative of one-dimensional heat flow into a semi-infinite medium;

c) determining pixel contrast data by subtracting said temperature versus time data standard from acquired pixel intensity data to develop temperature-time contrast data for at least one pixel; and d) determining actual thickness at a resolution element of the object corresponding to the pixel using said contrast data, said determination based on a heat-flow invariant relationship between an inflection point in the contrast data and a heat-flow characteristic time dependent upon thermal diffusivity of the object.

11. The method of claim 10 wherein the temperature versus time data standard, $T_s(t)$, is calculated according to the following formula:

$$T_s(t)=A[t^{1/2}-(t-\tau)^{1/2}]$$

where A is a parameter selected to match actual temperature on an object surface at a location corresponding to a selected analysis pixel in an acquired IR image, $\tau$ is a duration of heating the object before acquiring image frames and t is time.

12. The method of claim 10 wherein the object is rapidly heated using a flash lamp device.

* * * * *